United States Patent [19]
Fecht et al.

[11] Patent Number: 4,842,589
[45] Date of Patent: Jun. 27, 1989

[54] INTERCAVITY CATHETER

[75] Inventors: David C. Fecht, Manchester; Thomas B. Ferguson, St. Louis; Ronald Crouther, Chesterfield; Alan B. Ranford, St. Louis, all of Mo.

[73] Assignee: Sherwood Medical Company, St. Louis, Mo.

[21] Appl. No.: 935,378

[22] Filed: Nov. 26, 1986

[51] Int. Cl.$^4$ ............... A61M 25/00; A61B 17/28
[52] U.S. Cl. .................... 604/280; 128/321
[58] Field of Search ......... 604/272, 280, 93, 264, 604/177, 283, 273, 43, 45, 281; 128/328, 329 R, 305, 321

[56] References Cited

U.S. PATENT DOCUMENTS

| | | | |
|---|---|---|---|
| 2,458,305 | 1/1949 | Sanders | 604/282 |
| 3,140,715 | 7/1964 | Whitton, Jr. et al. | 128/321 |
| 3,169,527 | 2/1965 | Sheridan | 128/349 |
| 3,190,290 | 6/1965 | Alley et al. | 604/280 |
| 3,295,527 | 1/1967 | Alley et al. | 604/280 |
| 3,367,336 | 2/1968 | Eizenberg | 128/321 |
| 3,508,554 | 4/1970 | Sheridan | 128/348 |
| 3,589,368 | 6/1971 | Jackson | 604/280 |
| 3,608,539 | 9/1971 | Miller | 128/329 |
| 3,815,609 | 6/1974 | Chester | 128/321 |
| 3,948,273 | 4/1976 | Sanders | 604/280 |
| 4,490,139 | 12/1984 | Huizenga et al. | 604/272 |
| 4,496,353 | 1/1985 | Ouerland et al. | 604/270 |
| 4,548,602 | 10/1985 | Ring | 604/280 |
| 4,662,372 | 5/1987 | Sharkany et al. | 128/321 |
| 4,681,570 | 7/1987 | Dalton | 604/281 |

*Primary Examiner*—C. Fred Rosenbaum
*Assistant Examiner*—Kathleen Daley
*Attorney, Agent, or Firm*—Stanley N. Garber; Andrew J. Beck; William R. O'Meara

[57] ABSTRACT

An intercavity catheter having a distal end portion with serrations on the inner wall thereof.

9 Claims, 1 Drawing Sheet

INTERCAVITY CATHETER

FIELD OF THE INVENTION

The present invention relates to intercavity or intervessel catheters such as intercostal catheters which are inserted into a patient and the proximal end drawn out of the patient through a second incision or stab wound.

BACKGROUND OF THE INVENTION

Intercostal catheters such as mediastinal and thoracic catheters are used during surgical procedures to provide for wound drainage after the surgery. For example, the proximal end of a thoracic catheter may be inserted into the patient through the original incision and with the use of forceps or a hemostat pulled through a second incision or stab wound so that the distal end moves into a desired position within the wound area. A drain tube is then connected between the proximal end and a drainage collector. U.S. Pat. No. 3,295,527 describes the use of an intercostal catheter and is hereby inserted herein as a reference for disclosing the method of using an intercostal catheter.

One of the problems related to the use of such catheters is that when the hemostat is clamped against the proximal tip while pulling the proximal end through body tissue toward the outside of the body, the forceps often slips making it difficult to pull the proximal end of the catheter to the outside. This causes repeated clamping of the top and increases the chance of damage to the patient.

SUMMARY OF THE INVENTION

It is an object of the present invention to provide an improved intercostal catheter which obviates or reduces the above-mentioned problems or disadvantages. Another object is to provide a catheter that can be readily be grasped by forceps with reduced slippage between the forceps and the catheter. In accordance with one aspect of the present invention, a catheter is provided with a roughened area on the inner wall of the catheter adjacent the proximal end thereof for engagement with forceps during use of the catheter. In accordance with another aspect of the present invention, a plurality of laterally extending serrations are provided on the inner wall of the catheter adjacent the proximal end.

DESCRIPTION OF THE PREFERRED EMBODIMENT

Figure 1:
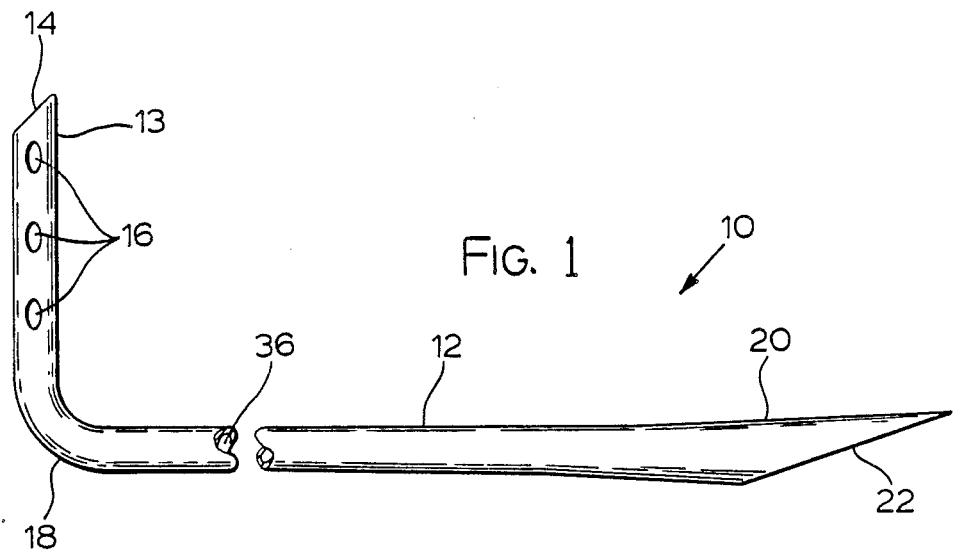
FIG. 1 is a side view of an intercostal catheter made in accordance with the present invention.

Referring now to the drawings and particularly to FIG. 1, an intercostal catheter, such as a thoracic catheter, is indicated generally at 10. Catheter 10 includes a flexible catheter body 12 having a distal end portion 13 with an open distal tip 14 formed at an angle to the longitudinal axis of the end portion 13. Distal end portion 13 is provided with a plurality of drainage inlet openings 16. The distal end portion is shown having a preset curve at 18 so that it extends at 90° to the rest of the body 12. The catheter 10 has a proximal end portion 20 in the form of a tube connector, that is, the proximal end portion tapers proximally radially outwardly so that it can subsequently be connected with another tube such as a drain tube received within the proximal end. The proximal end 20 has a tip end surface 22 formed at an angle, such as a 15° angle with respect to the longitudinal axis of the proximal end of the catheter 10.

Figure 2:
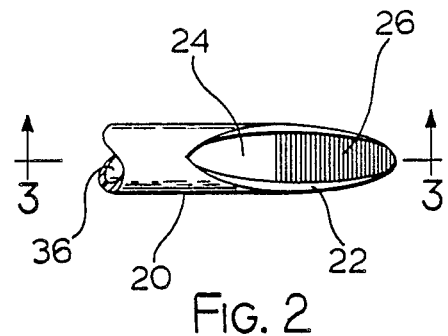
FIG. 2 is a fragmentary view of the proximal end of the catheter of FIG. 1 rotated 90°.
Figure 3:
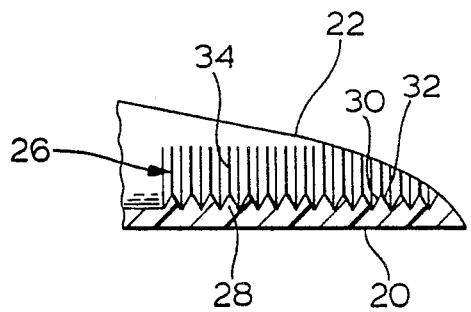
FIG. 3 is an enlarged cross-sectional view taken along the line 3--3 of FIG. 2.

As seen in FIGS. 2 and 3, the inner wall 24 of the catheter at the proximal end 20 is provided with a roughened surface area 26. Roughened surface 26 is preferably formed of a plurality of arcuate serrations 28 as best seen in FIG. 3. These serrations may be formed, for example as shown, in the form of teeth having equal opposed sides 30 and 32 with an included angle of 60°, each side being at a 30° angle with vertical passing through the of the sides. The sides of each serration intersect each other at a relatively sharp edge 34. The serrations are arcuate and extend distally inwardly, for example, for about 11/16 of an inch. The roughened surface may extend, for example, between ⅜ and 1 inch. The entire rest of the inner wall of lumen, indicated at 36, of the catheter is smooth, the serrations being preferably formed only at the proximal end portion.

In use, the proximal end may be inserted as the lead end into an original surgical opening in the body and then inserted from inside the body into a secondary incision or stab wound and then with a hemostat or forceps grapped and pulled out of the body through the secondary incision. The forceps or hemostat is also prefebably provided with similar serrations. By forming the catheter with serrations 28 of similar pitch to the pitch of the serrations on the forceps, the clamping of the forceps causes the serrations of the forceps to enter the grooves of the serrations whereby little or no slipping between the forceps and the catheter occurs when the forceps pull the catheter through the body of the patient. Forceps having serrations of a pitch different from that of serrations 28 will of course also provide good slippage resistance.

Catheter 10 may be formed or extruded of a suitable plastic such as polyvinyl chloride. The serrations may be formed by providing a mandrel formed with serrations complementary to the serrations shown in FIG. 3 and clamped against the inner wall at the proximal end of the catheter and heated to thereby heat-form the serrations. For example, the mandrel may be induction heated to cause the formation of the serrations and then the heat removed and a jet of cool air blown on the serrations to solidify them.

Although the invention has been described with reference to the preferred embodiment illustrated in the drawings, many modifications will be apparent to those skilled in the art without departing from the spirit or scope of this invention.

What is claimed is:

1. A catheter adapted to have one end pulled through an incision from inside a body to the outside of the body comprising a tubular member having a distal end portion for placement within the body, and a proximal end portion adpated to be grasped by forcep means and pulled through an incision in the body for subsequent positioning outside of the body, the inner wall of said proximal portion having a roughened area including a plurality of serrations adapted to be grasped by the forcep means during use, said roughened area extending distally substantially from the proximal most point of said proximal end portion for a predetermined distance, and the inner wall of the rest of said tubular member being substantially smooth.

2. The catheter of claim 1 wherein each of said serrations includes a pair of side walls intersecting each other defining an arcuate edge.

3. The catheter of claim 1 wherein said roughened area extends proximally between about one-quarter inch to one inch from the proximal most point of said proximal portion.

4. The catheter of claim 1 wherein the walls of said catheter between said roughened area and the distal most point of the tubular member being smooth.

5. The catheter of claim 1 wherein said tubular member is of a plastic material.

6. The catheter of claim 5 wherein said plastic material is a heat-formable plastic material.

7. The catheter of claim 6 wherein said plastic material includes polyvinyl chloride.

8. The catheter of claim 1 wherein said serrations are in substantially parallel arcuate rows.

9. The catheter of claim 1 wherein said proximal end portion has a proximal end edge which extends at an angle to the longitudinal axis of said proximal end portion.

* * * * *